(12) United States Patent
Akdis et al.

(10) Patent No.: US 8,512,012 B2
(45) Date of Patent: Aug. 20, 2013

(54) PUMP

(75) Inventors: Mustafa Akdis, Aachen (DE); Helmut Reul, Düren (DE); Sylvia Ruth Reul-Freudenstein, legal representative, Dëren (DE); Michele Lenz, legal representative, Frankfurt (DE); Jan Reul, legal representative, Düren (DE); Julian Paul Reul, legal representative, Düren (DE)

(73) Assignee: Circulite, Inc., Teaneck, NJ (US)

( * ) Notice: Subject to any disclaimer, the term of this patent is extended or adjusted under 35 U.S.C. 154(b) by 730 days.

(21) Appl. No.: 11/084,452

(22) Filed: Mar. 18, 2005

(65) Prior Publication Data
US 2006/0024182 A1   Feb. 2, 2006

(30) Foreign Application Priority Data

Mar. 18, 2004 (DE) .......................... 10 2004 013 746
Mar. 18, 2004 (DE) .......................... 10 2004 013 747
Apr. 20, 2004 (DE) .......................... 10 2004 019 721

(51) Int. Cl.
*F04B 35/04* (2006.01)
(52) U.S. Cl.
USPC .................. 417/423.12; 417/53; 415/900
(58) Field of Classification Search
USPC .............. 417/420, 423.12, 53; 415/58.4, 415/116, 111, 118, 229, 900; 604/151, 264; 600/600, 17
See application file for complete search history.

(56) References Cited

U.S. PATENT DOCUMENTS

| | | | |
|---|---|---|---|
| 3,771,910 A * | 11/1973 | Laing | 417/420 |
| 4,172,690 A | 10/1979 | Kuntz | |
| 4,688,998 A * | 8/1987 | Olsen et al. | 417/356 |
| 5,112,200 A | 5/1992 | Isaacson et al. | |
| 5,211,546 A | 5/1993 | Isaacson et al. | |
| 5,385,581 A | 1/1995 | Bramm et al. | |
| 5,405,251 A * | 4/1995 | Sipin | 417/420 |
| 5,443,503 A * | 8/1995 | Yamane | 623/3.14 |
| 5,470,208 A * | 11/1995 | Kletschka | 417/356 |
| 5,507,629 A * | 4/1996 | Jarvik | 417/423.3 |
| 5,695,471 A * | 12/1997 | Wampler | 604/131 |

(Continued)

FOREIGN PATENT DOCUMENTS

| | | |
|---|---|---|
| DE | 101 08 810 | 11/1977 |
| DE | 26 18 829 | 11/1997 |

(Continued)

OTHER PUBLICATIONS

Dec. 20, 2004 German Search Report (in English) for German Application No. 10 2004 019 721.0.

(Continued)

*Primary Examiner* — Devon Kramer
*Assistant Examiner* — Amene Bayou
(74) *Attorney, Agent, or Firm* — Wood, Herron & Evans, L.L.P.

(57) ABSTRACT

A pump and a method for operating a pump is proposed for mounting an impeller, which is inexpensive, free from contact and wear and thus extremely permanent. For this the invention uses a combination of permanent magnetic bearings and flow-mechanical bearings. The mounting is thus based on purely passive elements without using actively controlled and/or regulated elements.

49 Claims, 2 Drawing Sheets

(56) References Cited

U.S. PATENT DOCUMENTS

| | | | |
|---|---|---|---|
| 5,840,070 A | 11/1998 | Wampler | |
| 6,053,705 A | 4/2000 | Schöb et al. | |
| 6,071,093 A * | 6/2000 | Hart | 417/424.2 |
| 6,074,180 A * | 6/2000 | Khanwilkar et al. | 417/356 |
| 6,116,862 A | 9/2000 | Rau et al. | |
| 6,135,710 A * | 10/2000 | Araki et al. | 415/206 |
| 6,176,848 B1 * | 1/2001 | Rau et al. | 604/264 |
| 6,206,659 B1 * | 3/2001 | Izraelev | 417/420 |
| 6,227,797 B1 * | 5/2001 | Watterson et al. | 415/107 |
| 6,227,817 B1 | 5/2001 | Paden | |
| 6,227,820 B1 * | 5/2001 | Jarvik | 417/423.12 |
| 6,234,772 B1 * | 5/2001 | Wampler et al. | 417/423.12 |
| 6,234,998 B1 * | 5/2001 | Wampler | 604/131 |
| 6,293,901 B1 * | 9/2001 | Prem | 600/17 |
| 6,394,769 B1 * | 5/2002 | Bearnson et al. | 417/423.7 |
| 6,527,699 B1 * | 3/2003 | Goldowsky | 600/16 |
| 6,595,762 B2 * | 7/2003 | Khanwilkar et al. | 417/423.7 |
| 6,607,370 B2 * | 8/2003 | Fukamachi et al. | 417/420 |
| 6,623,475 B1 | 9/2003 | Siess | |
| 6,717,311 B2 * | 4/2004 | Locke | 310/90.5 |
| 6,908,280 B2 * | 6/2005 | Yamazaki | 415/206 |
| 6,966,748 B2 * | 11/2005 | Woodard et al. | 415/104 |
| 2001/0031210 A1 * | 10/2001 | Antaki et al. | 417/356 |
| 2004/0115038 A1 | 6/2004 | Nuesser et al. | |
| 2008/0091265 A1 | 4/2008 | Nuesser et al. | |

FOREIGN PATENT DOCUMENTS

| | | |
|---|---|---|
| DE | 298 21 565 | 6/2000 |
| DE | 100 16 422 A1 | 10/2001 |
| EP | 0 599 138 | 6/1994 |
| EP | 0 900 572 | 3/1999 |
| EP | 0 904 117 | 7/2000 |
| JP | 2002 315824 | 10/2002 |
| WO | WO 96 00335 | 1/1996 |
| WO | WO 96 31934 | 10/1996 |
| WO | WO 98/11650 | 3/1998 |
| WO | WO 02/066837 | 8/2002 |

OTHER PUBLICATIONS

International Search Report of PCT/DE2005/000494.

English translation of International Preliminary Report on Patentability in PCT/DE2005/000494.

* cited by examiner

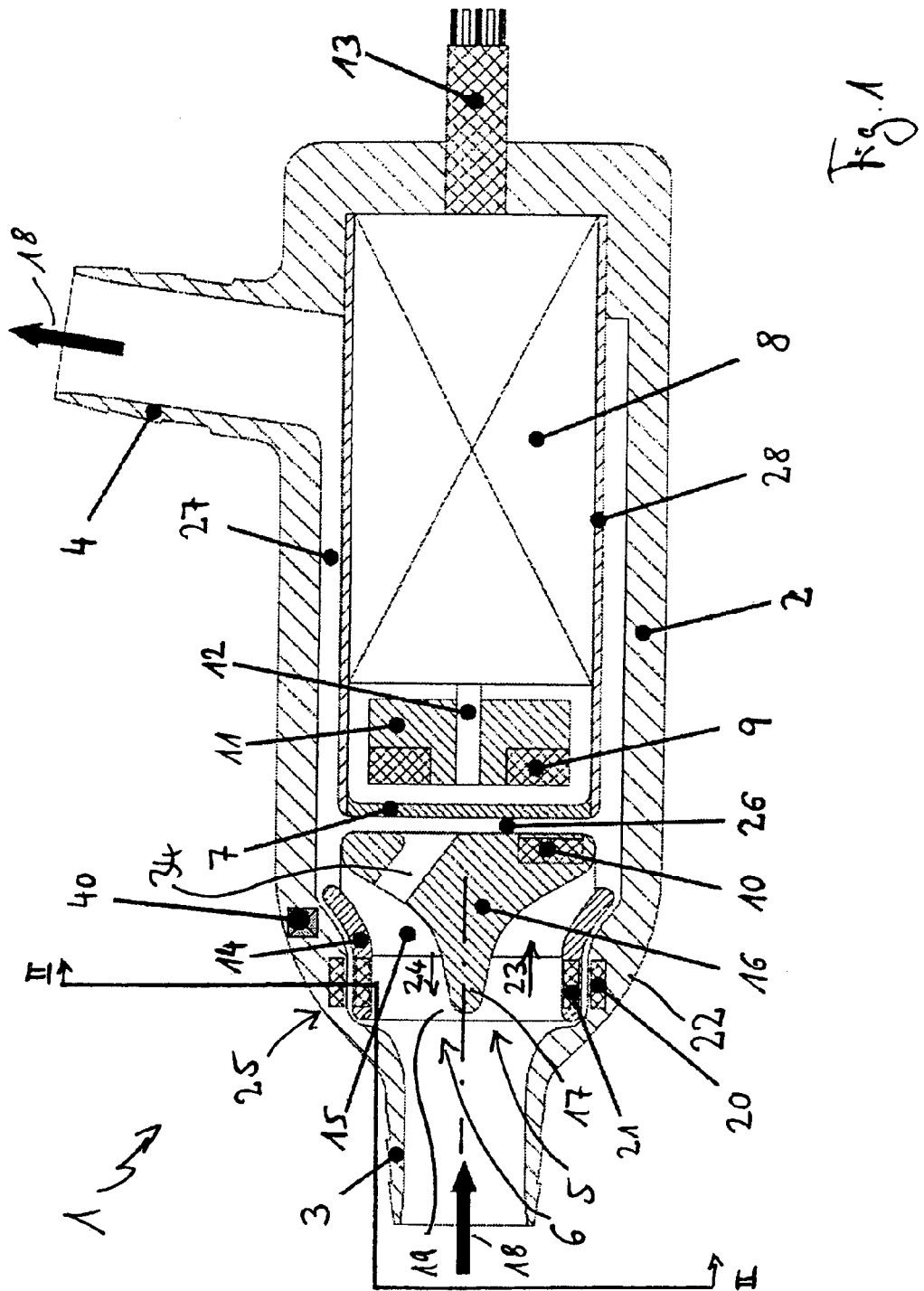

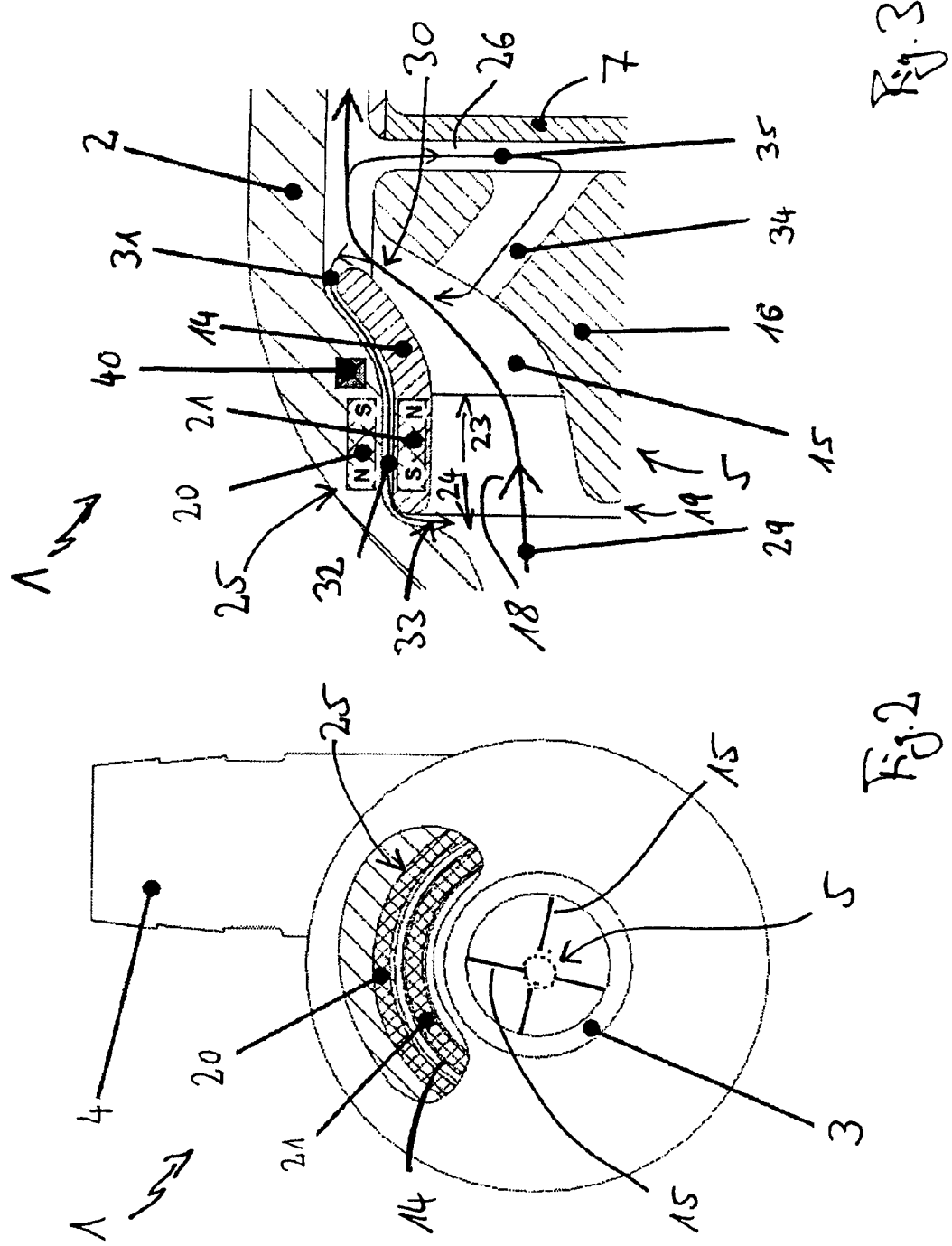

PUMP

CROSS REFERENCE TO RELATED APPLICATIONS

Applicant claims priority under 35 U.S.C. §119 of German Application No. 10 2004 013 747.1 filed on Mar. 18, 2004; German Application No. 10 2004 013 746.3 filed on Mar. 18, 2004; and German Application No. 10 2004 019 721.0 filed on Apr. 20, 2004.

TECHNICAL FIELD

The application relates to a pump. The invention especially relates to a pump for conveying blood.

BACKGROUND

Numerous impeller pumps are known from the prior art, wherein the impellers are mostly guided mechanically, in some cases also free from bearings. Reference is made to various documents as examples for the field of medical technology:

U.S. Pat. No. 6,116,862 discloses a blood pump with an impeller wheel which is mounted on ball bearings in the axial direction and is centred in the radial direction by a star-shaped cross-member.

EP 0 904 117 B1 discloses a blood pump wherein an impeller is also fixed axially by means of a ball bearing. Radial alignment is provided by means of a friction bearing on a shaft of an impeller or by means of magnets installed on a preliminary housing which is connected to a main housing of the pump by means of a cross-member.

DE 100 16 422 A1 discloses a blood pump which has an impeller fixedly installed in a housing.

In EP 0 599 138 A2 an impeller of a blood pump is arranged on a shaft projecting into a separate housing.

U.S. Pat. No. 5,840,070 discloses a rotor on a shaft wherein alignment is provided by numerous magnets both on impellers of the motor and on the shaft.

DT 26 18 829 A1 discloses a multi-stage centrifugal pump in which the individual pump stages are made of plastic and are deformed by axial pre-stressing wherein side walls of individual stage housings are pressed towards a casing to achieve a tight connection there.

DT 298 21 565 U1 discloses a bearing-free blood pump. An impeller is driven by a magnetic coupling which produces an axial attraction of the impeller to the motor. The impeller can move freely in a pump housing within a limited tolerance and conveys blood in an axial outflow direction when the impeller is driven. The impeller imparts a momentum to the blood to deflect the axially inflowing blood through 90° to a radial outflow. The blades of the impeller have bearing surfaces on their side facing away from the inflow so that the rotating impeller does not make contact axially with the housing as a result of the counter momentum.

U.S. Pat. No. 5,385,581 discloses a blood pump with pure magnetic bearings which support an impeller with an electromagnetic mounting device free from contact. An electronic measuring and control system is provided for this purpose, resulting in a bulky design as a consequence of the complex mounting. In addition, additional energy must be supplied for active centring of the impeller.

Berlin Heart AG has developed an implantable heart support system in the form of an axial pump. This is available on the market under the name INCOR (registered trademark). An impeller rotates in suspension, free from any contact, as a result of a magnetic bearing and takes over the actual pumping function at speeds of up to 12,000 rpm. This corresponds to a possible blood flow of 7 l/min against 150 mmHg. A stationary diffuser wheel positioned after the impeller takes the rotary movement out of the rotating blood, builds up additional pressure and transports the blood to the aorta. The magnets of the axial pump are connected to control electronics for the contact-free mounting of the impeller so that the magnetic field strength can be quickly adapted to a changed position of the impeller over time. The pump has an electrical power consumption of 8.5 W. A running time of about 12 hours is achieved using an external power pack. The object of the invention is to provide a particularly inexpensive, energy-saving and low-wear pump.

With regard to the possible use in medical technology as a blood pump, for example, as a microdiagonal blood pump, the invention additionally relates to further aspects: according to the prior art it is usual for centrifugal pumps to use at least one mechanical friction bearing liable to wear for mounting the impeller. As part of in-vivo studies where these types of blood pumps were tested, problems with the formation of blood clots in the inflow area to the pump were seen again and again. In studies using blood thrombus depositions were found on cross-members for fixing the impeller on an upstream side. With reference to the application in medical technology, it is the object of the invention to provide a blood pump in which thrombus deposition in the inflow area of the pump is reliably avoided with a high degree of reliability using means which can be manufactured very cheaply. At the same time, the pump should be free from wear.

SUMMARY OF THE INVENTION

The objects are solved by a pump comprising an impeller having an axis of rotation in a pump housing and comprising an axial inflow channel to the impeller, wherein the pump is distinguished by a magnetic axial bearing and a flow-mechanical radial bearing for operating the pump without contact between the impeller and the housing.

According to the invention, the impeller is thus guided simultaneously by a flow-mechanical bearing and a magnetic bearing such that during operation any touching or impact of the impeller on the pump housing or of the impeller on other stationary parts of the pump is avoided. An excellent property of this hybrid bearing is based on the possibility of using exclusively passive bearing elements, that is no active control and regulating elements such as sensors and actuators are required for the functional efficiency of the mounting.

Compared to the blood pump from DE 298 21 565 U1 which is also free from bearings, the pump proposed in the present case is characterised by the fact that the axial mounting is at least predominantly provided by magnetic forces wherein in the cited utility model specification the axial mounting is provided hydrodynamically. Compared to this, the solution proposed in the present case has the major advantage that axial impact of the impeller on the pump housing is reliably avoided even when starting the pump from stationary. In DE 298 21 565 U1, on the other hand, the impeller rests against the pump housing when the blood pump is stationary. When the impeller starts to rotate, the blades therefore initially scrape over the bottom of the housing.

The present invention implements the finding that axial impact or scraping of the impeller on the pump housing can have considerable effects on the lifetime and operating safety of the pump. Thus, axial securing of the impeller is achieved in the present case using a magnetic bearing whereas radial stabilisation is accomplished at least also by a flow-mechanical bearing. According to a further aspect of the invention, the object is also solved by a pump comprising an impeller having an axis of rotation in a pump housing with an axial inflow channel to the impeller, wherein the pump is distinguished by a combined axial and radial bearing on a circumference of the impeller for operating the pump without contact between the impeller and the housing.

According to this aspect of the invention, an impeller mounting can be manufactured especially cheaply by providing a combined bearing on the circumference of the impeller. It is particularly advantageous if the combined axial and radial bearing provides the axial stabilisation of the impeller by means of magnets and the radial stabilisation of the impeller by means of a flow-mechanical bearing during operation of the pump.

In addition to the cost savings made possible by a combined bearing, the pump can also be made particularly small. Thus, both proposed pumps are especially suitable for use in a centrifugal blood pump, especially as a blood pump for conveying blood.

The passively acting magnetic axial bearing can be manufactured particularly simply using permanent magnets. In particular, the use of neodymium-iron-boron (NdFeB) is proposed for this purpose. Particularly suitable for the magnetic axial bearing are two permanent-magnetic rings, of which advantageously one stator magnet can be integrated in the pump housing so that it does not move whilst a rotor magnet of the magnetic axial bearing is integrated in a sleeve around the impeller and is linked to its rotation. In this way, both permanent magnets can be held outside the actual flow paths wherein nevertheless, a short distance can be achieved between the stator magnet and the rotor magnet.

Independently hereof, it is proposed that especially the magnetic axial bearing exerts a tilt restoring force against any tilting of the impeller with respect to a plane normal to the principal axis. The axial bearing is particularly suitable for this purpose since any tilting of the impeller in the manner described always brings about an axial displacement of the circumference which can be determined on the circumference of the impeller. If the axial bearing on the circumference of the impeller in each case locally brings about an axial restoring force in the event of deflection, this also means that the same magnetic bearing provides a tilt restoring moment during tilting movements of the impeller. The effect of this restoring moment can be further supported when a flow-mechanical radial bearing is simultaneously present. Such a mounting of the impeller against axial displacements and lateral tilting can simply be provided by a passively acting permanent magnetic bearing.

In a preferred embodiment of the proposed pump with a magnetic axial bearing, a rotor magnet and a stator magnet of the magnetic axial bearing are magnetised in the axial direction, the stator magnet being magnetised in the opposite direction to the rotor magnet. In particular, if the ring magnets are arranged concentrically, this yields a force of attraction between the two magnetic rings which acts both in the axial and in the radial direction. The axially attractive force of this configuration brings about a stable mounting of the rotor magnet inside the stator magnet such that the impeller is stabilised both against any axial displacement and against tilting movements. The stability of the mounting and the tilting direction is based on the attractive restoring forces which are active between the two magnetic rings and strive to continuously move the rotor magnet back into the central position of the stator magnet.

For safe and wear-free operation of the pump it is proposed that the passive magnetic axial mounting is designed such that the axially attracting forces between a rotor magnet and a stator magnet over at least most of the axial play of the impeller are always greater than the attractive magnetic forces acting downstream in a magnetic coupling between the impeller and a drive. Such a design is characterised by the fact that a downstream axial deflection of the impeller under the bilateral influence of the magnetic field of the magnetic axial mounting and the magnetic coupling brings about a resulting restoring force upstream i.e., against the downstream deflection. The axially upstream restoring force of the magnetic axial bearing is therefore greater than the axially downstream deflection force produced by the magnetic coupling. This equally ensures that the tilt restoring forces of the magnetic mounting are always greater than the forces acting in the magnetic coupling in the event of an initial deflection of the impeller. The design of the bearing and coupling magnets described has the direct result that the impeller is always mounted without any contact in the axial direction. This directly corresponds to one aspect of the invention since in this way the impeller never has any axial contact with the stationary pump housing or the motor cover. This freedom from axial contact occurs both when the impeller is stationary and when the pump is operating. Any wear caused by axial contact is hereby avoided; rather the impeller experiences axial equilibrium in the influence of the magnetic coupling and the magnetic axial bearing axially downstream from the stator magnet of the magnetic axial mounting but significantly before any impact of the impeller at the downstream boundary of its play by the housing, i.e., usually at the magnetic coupling.

It is advantageous if the axial restoring force takes place in the event of an axial deflection of up to 1 mm, preferably of up to 3 mm, especially preferably of up to 5 mm.

It is explained that the expressions "upstream" and "downstream" used to illustrate a relative position make an unconditional reference to an operating situation of the pump from the wording. However, these relative positional details should also be identified outside an operating state of the pump. Thus, both details always relate to an axial position relative to the axis of rotation of the impeller, where "upstream" always lies closer to the axial inflow channel to the impeller than "downstream".

Whereas in pumps known so far a motor cover always exerted a bearing function, mostly as a support for a ball bearing but also as in DE 298 21 565 U1 as a flow-mechanical axial bearing, the motor cover in a pump according to the present invention merely serves as a partition between a motor chamber and a blood chamber. This has the advantage that the motor cover is not exposed to any significant mechanical stresses. In view of this and in order to avoid any eddy current effects in the intermediate space of the magnetic coupling and heating of the motor cover associated therewith, it is proposed that said cover should be made of a non-metallic and/or a non-magnetic material, for example, of a biocompatible plastic or titanium.

It is known from magnet teaching that a body cannot be held stably in space merely by means of passive magnetic forces. At least one of the six spatial degrees of freedom of the body behaves very unstably in a passive magnetic field. The stable state of suspension of the body always requires active controlled magnetic forces or additional bearings which eliminate the unstable degree of freedom. In the case of the proposed magnetic axial bearing such that axial fixing is accomplished by the passive magnetic forces, the unstable degree of freedom is the radial freedom of movement of the impeller. According to one finding of the invention, however no increased wear is caused if the impeller is in radial contact with the housing when stationary as long as this is lifted during operation. When the impeller is started up from stationary, only very small radial forces occur compared with the axial forces, especially as a result of the deflection of the flow. Thus, the impeller, when starting up, can almost immediately become released from radial contact with the housing and take up a stable position in the pump brought about by the flow mechanics.

The stabilisation of the impeller in the radial direction and thus the taking up of the completely contact-free rotor mounting during operation can preferably be accomplished by using an eccentric annular gap around a deflected impeller. If a magnetic axial bearing is provided with two rings magnetised axially in opposite directions, a radial deflection of the impeller at the height of the magnetic axial mounting is further intensified by the unequal radial proximity between stator magnet and rotor magnet. During operation a secondary flow must therefore be adjusted for a flow-mechanical radial bearing so that the flow-mechanical radial bearing exerts a radial restoring force on the impeller when the impeller is deflected which is greater than the radial force of the magnetic axial bearing which drives the deflection further. In this situation, the flow-mechanical radial bearing can be supported by an additional centring effect of a magnetic coupling.

At the same time, care should be taken alternatively and cumulatively to ensure that a principal flow, a magnetic coupling and a magnetic axial bearing can be adjusted with respect to one another so that the impeller acquires a stable axial equilibrium even if axially downstream impulses act on the impeller in a time-constant or fluctuating fashion wherein axial movements of the impeller can especially be restricted to a few millimeters without a stable mounting becoming unstable.

A flow-mechanical radial bearing is very cheap to implement because the centring of the impeller can take place automatically if the flow-mechanical radial bearing is suitably designed. This takes place if, in the event of the impeller being deflected into that range where the impeller approaches a housing wall, a restoring force exceeding the deflection force is exerted on the impeller until this is centred again in the inflow channel. The restoring force as a centring force can especially be exerted on a circumference of the impeller.

In order to achieve a reliable flow-mechanical bearing effect, it is advantageous if an annular sleeve surrounding the impeller and fixed thereto is provided inside a surrounding wall of the pump housing. An annular sleeve coupled to the rotation of the impeller, which runs around the impeller, makes the pump of a flow-mechanical mounting particularly accessible, especially upstream of the impeller, especially preferably at about the axial height of an upstream beginning of the impeller. As a result of the rotation of the annular sleeve during rotation of the impeller, the probability of flow dead areas at the annular sleeve is also largely eliminated. In addition, a flow-mechanical bearing can exert restoring forces particularly effectively at the circumference of the annular sleeve.

It may be noted that flow-mechanical bearings proposed as part of this application can also include the special case of a hydrodynamic mounting and another fluid film mounting.

It is proposed that in addition to an axial and/or diagonal-axial principal flow channel through the impeller and the axial inflow channel to the principal flow channel of the impeller, the pump has a secondary channel, wherein the secondary channel has a supply opening and a discharge opening or which the discharge opening is oriented towards the inflow channel. When suitably designed, the secondary channel forces a secondary flow of such an intensity that the flow through the secondary channel can be used for the flow-mechanical mounting of the impeller. The bearing flow can be guided separately from the main flow during its passage in the secondary channel and in particular it can run oriented substantially in the opposite direction to the principal flow through the impeller. This makes it possible for fluid to circulate automatically through the flow-mechanical radial bearing without the need for branching from the principal flow.

It is proposed that during operation of the pump the bearing flow is supplied from the outflow from the impeller. The energy level of the pumped fluid is particularly high immediately on leaving the impeller, so that a pressure difference prevails compared with an upstream point, which can be used to produce the secondary flow.

In order to make the best possible use of the energy gradient, the secondary flow can discharge into the inflow from the impeller. The energy level of the pumped fluid is at its lowest immediately before the impeller.

It is noted that a pump comprising an impeller, especially a blood pump with a bearing flow running substantially in the opposite direction to a principal flow during operation, in combination with a magnetic axial bearing is advantageous and inventive regardless of all the remaining features of the present invention. The same applies to a pump, especially a blood pump, wherein a bearing flow from an outflow from the impeller is stored during operation and to a pump, especially a blood pump wherein a bearing flow discharges into an inflow to the impeller during operation.

In a preferred embodiment a secondary channel, extended flat and in one dimension perpendicular to its surface is more than 100 μm wide, preferably about 300 to 700 μm, especially preferably about 500 μm. Classical hydrodynamic friction bearings intercept the forces acting on a rotor by a compressive force produced in a flow-mechanical lubricant film. For this purpose the thickness of the lubricant film must be so small that the viscous forces exceed the inertial forces.

Usual gap widths are around 10 μm. Only then can the forces produced in the viscous lubricant film keep the external forces acting on the rotor in equilibrium and prevent radial impact of the rotating part on the housing.

As long as mixed friction is avoided, the mounting remains free from wear. The important disadvantage of such a pure hydrodynamic radial mounting for application in a blood pump however is that the small-width of the lubricant gap significantly increase the shear stresses and thus the haemolysis rate of the blood pump and therefore restricts usage in patients which must gentle on the blood. In addition, with such small gap widths there is an increased risk of flow dead regions so that the risk of thrombus deposition in the bearing area is increased, which must be avoided in blood pumps for long-term use. However, the present invention can be used in a flow-mechanical mounting with significantly larger gap widths, especially with gap widths up to around 500 μm. This considerably reduces the risks of haemolysis and thrombogeneity.

In the course of expensive experiments on flow guidance, it has also been shown that it is advantageous if the bearing flow runs predominantly axially in a tangentially and axially extended secondary channel during operation. The secondary channel can especially be an annular gap.

It is expressly noted that a blood pump with a flow-mechanical radial bearing flow running predominantly axially in a tangentially and axially extended secondary channel is advantageous and inventive in itself in combination with a magnetic axial bearing, especially if the secondary channel is an annular gap around the impeller. The same applies to a blood pump with a secondary channel for a flow-mechanical mounting wherein the secondary channel has a gap width of more than 100 μm, preferably of around 300 μm to 700 μm, especially preferably of about 500 μm.

Alternatively and cumulatively to the aforesaid, it is proposed that the radial bearing flow during operation accounts for between 5% and 50%, preferably between 10% and 50%, particularly about 30% of a principal flow. It has been found that when the flow is adjusted within this range, a sufficient flow-mechanical radial cushion can be produced for the impeller and flow stagnation in the secondary channel can be reliably avoided. Flow rates of the principal flow between 1 l/min and 10 l/min, particularly around 5 l/min, are especially suitable for a blood pump.

It is proposed that the annular gap is designed so that when the impeller is radially centred, there is no radial contact between the impeller and a surrounding wall of the pump housing. Independently hereof, a discharge opening of the secondary channel in the axial direction can be covered by a radial projection from the pump housing. The advantage of a circumferential annular gap around the impeller is the wear-free mounting wherein a projection of the housing can precisely cover the discharge opening of the secondary channel so that despite the circumferential opening, the principal flow does not flow in an uncontrollable fashion through the secondary channel.

In addition to the flow-mechanical radial bearing, a mechanical radial limitation of play can also be provided for the impeller.

A secondary channel having an axial length of 1 mm to 20 mm, preferably of around 5 mm, is especially suitable for use in blood pumps. A diameter of 2 mm to 100 mm, preferably of 15 mm to 25 mm, especially preferably of about 20 mm is proposed for the dimensions of the impeller.

Independently hereof, it is proposed that the impeller is driven at a speed of less than 50,000 rpm, preferably between 2000 and 10,000 rpm, especially at around 5000 rpm.

Independently hereof, it is proposed that as a device for increasing the flow energy of fluid flowing through the principal flow channel of the pump is provided between a feed opening and a discharge opening of the secondary channel. In this way, a significant pressure gradient can be produced between feed and discharge of the secondary channel which makes the flow direction of the fluid in the secondary channel reliably predictable. The device for increasing the flow energy can especially be the driven, rotating impeller itself.

The centring effect by the radial restoring forces at the flow-mechanical radial bearing can be supported by a magnetic coupling between a motor and the impeller. An axially attracting rotary face coupling between impeller and motor has a stiffness during axial deflection which strives to radially centre the coupling magnets on the impeller with respect to the magnets on the motor. The simultaneous action of the radial restoring forces of the flow-mechanical radial bearing on the one hand and of the magnetic coupling on the other contributes to the higher overall stability and quietness of the impeller.

By using this effect in the leakage area of the pump, the rotor can be radially stabilised without any mechanical friction bearings. Using the otherwise unavoidable internal losses of the pump to ensure functional safety makes the inventive proposal particularly economical. This economical aspect is emphasised still further by using radial forces in a magnetic coupling which are present in any case. In this case, the design can be extremely compact, especially if a rotor magnet and a stator magnet of the magnet axial bearing at least spatially enclose a part of a flow-mechanical radial bearing.

For completeness it is noted that the present invention also functions freely on a flow-mechanical radial bearing with a narrow bearing channel according to classical hydrodynamic lubrication theory. However, a larger gap width, especially up to 500 μm, is to be preferred for a blood pump. In this respect, the pump according to the present invention provides a particularly simple, reliable and inexpensive solution for a rotor mounting which is very gentle on the blood, with the possibility for replacing all mechanical bearings with contact-free bearings.

In a pump having a magnetic axial bearing and a magnetic coupling between impeller and motor, the impeller takes on an axial equilibrium between an uninfluenced state of rest on the magnetic axial bearing and an uninfluenced state of rest on the magnetic coupling when operating at constant inflow and when the magnets and channel geometry are suitably adjusted. When the inflow varies with time, for example, as a result of a pressure thrust during a heart beat when the pump is used in medical technology, a temporary force different from the quasi-static force of the principal flow builds up briefly upstream of the pump. The force difference perturbs the axial equilibrium of the impeller so that the impeller takes on a different axial position during the change in force. When the pump is operating, the contact-free suspended state of the impeller can be subjected to deflections, both the axial and the radial deflections being proportional to the forces acting on the impeller. When suitably adjusted, during operation of the pump the impeller therefore moves according to speed, pressure and flow conditions as well as external forces, for example as a result of the patient having a fall, freely in the conveying medium inside the pump housing without coming into contact with the pump housing.

According to an inventive finding, the movement of the impeller in the axial direction in particular is a measure for the flow forces acting on the rotor, which result from the pressure profile of the flowing fluid on the impeller. It is thus proposed that the pump has a sensor detecting the magnitude of the axial displacement of the impeller.

The sensor can especially detect the axial movements of the impeller without any contact, i.e., non-invasively, and thus give indications of the operating point of the pump. The displacement distance measured by the sensor is thus proportional to the pressure distribution at the rotor and can be correlated with the pump flux in conjunction with the hydraulic performance graph of the pump. For a non-invasive measurement the sensor preferably lies outside the channel network, especially separated from the channel network by a partition. The sensor can, for example, determine the displacement of the impeller capacitively, inductively or resistively. Direct access to the channel networks is thus unnecessary.

In a preferred embodiment an evaluation device is provided which calculates the pressure and/or flow velocity, especially the flow rate and in medical technology applications, for example, the heart rate inside the pump, from measured values of the sensor combined with known values for speed, voltage and flow and displays these numerically or alphanumerically. The invention at the same time provides the possibility for identifying anomalies in the heart rate such as extra-systole or ventricular fibrillations for example from the recorded sensor signals.

It is advantageous if the sensor signal recorded in this way is used as an input quantity for regulating the pump according to the physiological requirements. It can also be used for diagnostic purposes in the patient.

When a sensor is used, separate pressure and flow sensors which are in contact with the blood and are liable to drift during long-term use, can advantageously be completely dispensed with. The entire blood pump is therefore reliable with regard to long-term use in a patient and at the same time, handling and monitoring the pump functions is easy.

It is expressly noted that the provision of a sensor for detecting the magnitude of the axial displacement of the impeller in a housing of a blood pump, wherein the impeller preferably takes on contact-free equilibrium when the blood pump is operating and preferably also when it is stationary as a result of axial forces, is advantageous and inventive regardless of the other features of the invention.

BRIEF DESCRIPTION OF THE DRAWINGS

The invention is explained in further detail subsequently using an exemplary embodiment with reference to the drawings. Herein:

FIG. 1 is a longitudinal section showing a blood pump comprising a combined magnetic axial bearing and flow-mechanical radial mounting of an impeller and comprising a sensor, FIG. 2 shows the blood pump from FIG. 1 in a partially cutaway view as indicated by II-II in FIG. 1 and FIG. 3 shows the blood pump from FIGS. 1 and 2 with sections of the longitudinal section from FIG. 1 enlarged and flow paths identified schematically.

DETAILED DESCRIPTION

The blood pump 1 in FIGS. 1, 2 and 3 substantially consists of a pump housing 2 with an inlet channel 3 and an outlet channel 4. Located inside the pump housing 2 are an impeller 5 in a compartment 6 provided herefor and behind a motor cover 7 is a motor 8 for driving the impeller 5 via a magnetic coupling 9, 10. The coupling magnets 9 on the motor side are located in a pole shoe 11 arranged on a shaft 12 of the motor. A cable lead 13 runs to the motor 8 to drive said motor.

An annular sleeve 14 is provided on one circumference of the impeller 5. The annular sleeve 14 is connected to blades 15 of a central blade member 16 of the impeller 5 so that a rotation of the central blade member 16 about an axis of rotation 17 at the same time brings about just such a rotation of the annular sleeve 14 about the axis of rotation 17. Two permanent magnetic rings 20, 21 lie at an upstream end 19 of the impeller 5 in relation to a provided flow-through direction 18, arranged at its axial height. A stator magnet 20 is integrated in a wall 22 of the pump housing 2; a rotor magnet 21 is integrated in the annular sleeve 14 of the impeller 5 concentrically to the stator magnet 20 and in identical axial extension. The stator 20 and the rotor 21 are magnetised in the axial direction, the stator being magnetised in the opposite direction to the rotor (the magnetic poles are identified by "N" and "S"). It is noted that different lengths of stator and rotor magnet in their axial extension can be used. In this way, the range of stability of the mounting can be expanded.

The oppositely oriented magnetic rings, stator 20 and rotor 21, function as magnetic axial bearings. The coupling magnets 9, 10 mutually attract so that a force which accelerates the impeller 5 towards the motor cover 7 acts on the impeller 5. At the same time, however, such a displacement would displace the rotor 21 towards the stator 20 in an axial direction of deflection 23. By this means the S pole of the rotor is moved away from the N pole of the stator and the N pole of the rotor is moved away from the S pole of the stator and at the same time the S pole of the rotor is brought closer to the S pole of the stator. Consequently, the permanent magnetic rings, stator 20 and rotor 21, exert a force in an axial restoring direction 24. The axial restoring direction 24 is oppositely directed to the deflection 23 by the coupling magnets 9, 10. In this respect, the permanent magnetic rings, stator 20 and rotor 21, act as magnetic axial bearings 25 against an axial displacement of the impeller 5.

The restoring force 24 becomes increasingly larger with increasing displacement of the rotor 21 towards the stator 20 until the restoring force reaches a maximum at the point where the two S poles of the stator 20 and the rotor 21 come to lie under one another. However, a downstream bearing gap 26 is made so narrow that the two S poles of the rotor 21 and the stator 20 cannot come to lie under one another. Thus, the magnetic axial bearing 25 cannot be brought from its stable position by mechanical effects on the impeller 5.

As a consequence of the force of attraction between the coupling magnets 9, 10, however the impeller 5 adopts an equilibrium position (not shown in the drawing) in which the impeller 5 adopts and retains a displacement 23 with respect to an uninfluenced original position (shown in the drawing) of the magnetic axial bearing 25. The axial equilibrium position lies further away from the inlet channel 13 than is shown in the figures, i.e. downstream in the wording of the present application.

Whereas the impeller 5 lies inside the housing 2 axially free from contact, when the pump 1 is stationary, the annular sleeve 14 rests laterally against the wall 22 of the housing 2 since the stator 20 and the rotor 21 cannot achieve a stable mounting in the radial direction in addition to the axial magnetic contact-free mounting. Rather, the impeller 5 is deflected radially until it rests against the housing wall 22 through contact with the annular sleeve. This radially off-centre state is mechanically limited by the unequal spacing of the rotor 21 from the stator 20 over the circumference of the magnetic axial bearing. In the area of the magnetic coupling 9, 10 between the impeller 5 and the motor 8, the impeller 5 no longer rests on the housing 2 since this expands to form an annular principal flow-through channel 27 starting from the annular sleeve 14. The principal flow-through channel 27 passes-around the motor wall 28 as far as the outflow connecting piece 4.

As a result of the relatively stable position of the impeller 5 at the magnetic coupling 9, 10 with the simultaneously stable off-centre position of the impeller 5 at the magnetic axial coupling 25, the impeller 5 is deflected slightly with respect to the axis of rotation 17, in addition to a slight parallel displacement. This also effects a slight displacement of the poles between stator 20 and rotor 21 so that even in the stable off-centre state, the magnetic axial bearing 25 exerts a slight restoring force on the impeller 5. Consequently, only a small additional centring force is sufficient to centre again the annular sleeve 14 of the impeller 5 free from contact inside the housing wall 22.

When the pump is operating, the motor 8 drives the impeller 5 to rotate about the axis of rotation 17 via the magnetic coupling 9, 10. Inflowing blood flows in a principal flow 29 of about 5 l/min through the impeller 5 to the principal flow channel 27 and through the outlet connecting piece 4 out of the blood pump 1. Inside the impeller 5 the blood is outwardly deflected on the central blade member 16 and accelerated towards the outside as it runs over the blades 15 so that it leaves the impeller on an outflow 30 from said impeller in a diagonal direction and having a particularly high energy level. Through a feed opening 31 between the annular sleeve 14 and housing wall 22 on the outflow 30 from the impeller 5, blood enters into a bearing channel 32 again upstream from a discharge opening 33 of the bearing channel 32 and from there again enters the inflow 29 to the impeller 5. The pressure difference between the feed opening 31 and the discharge opening 33 of the bearing channel 32 is so large that about two fifths and therefore about 2 l/min of the blood flow will branch off as leakage flow and thus flow back substantially axially between the annular sleeve 14 and the housing wall 22. At the same time, a flow-mechanical radial bearing is formed in the bearing channel 32 and therefore also between the magnetic axial bearing 25. The magnetic axial bearing 25 is arranged in combination with the flow-mechanical radial bearing upstream of the blades to have a particularly good lever effect for restoring forces.

As a result of the blood flow being deflected inside the impeller 5, the blood has a flaring force on the impeller in the direction of displacement 24. However, the magnetic axial bearing is so strong that both the coupling attractive force 9, 10 in the direction 23 and the flaring force produced by the flow in the direction 24 do not outweigh the axial bearing force between the magnetic rings 20, 21. Thus, even when blood flows through the impeller 5, an axially contact-free equilibrium position of the impeller 5 inside the housing 2 is established. This equilibrium position during operation is only displaced by a certain amount upstream or downstream with respect to the equilibrium position when the impeller 5 is stationary (not shown in the diagram). When the inflow 29 fluctuates, the impeller 5 undergoes a brief axial deflection corresponding to the flow fluctuation; however, in all the pressure and flow states to be expected when used as a blood pump, the impeller remains axially free from contact with the housing 2 and the motor cover 7.

As a result of the flow-mechanical radial bearing, the annular sleeve 14 moves directly away from the housing wall 22 when the impeller starts up and takes on a stable position completely free from contact with the housing 2, even in the radial respect. In this situation the impeller 5 is mounted in the pump housing 2 by means of the magnetic axial bearing 25 and by means of the flow-mechanical radial bearing without contact between the impeller 5 and the housing 2 so that it can rotate stably. Consequently, a combined axial (25) and radial bearing stabilizes the impeller 5 on the circumference of the impeller 5, in the present case on the circumference of the annular sleeve 14. Any damage to the blood and thrombus formation is reliably avoided because the flow-mechanical friction bearing has a gap width of about 500 µm and no flow dead regions occur anywhere. Among other things, flushing holes 34 and a flushing flow 35 forcibly produced hereby in the central blade member 16 take care of this.

A sensor 40 is additionally provided in the wall 22 of the housing 2, which records any radial and axial displacement of the impeller 5 with a high degree of accuracy when the impeller 5 is displaced axially and/or radially inside the housing 2. The exact position of the impeller 5 in the housing 2 can be determined using the sensor signal from the sensor 40. This allows the flow conditions of the blood through the blood pump 1 and thus the operating state of the pump to be determined directly. For example, the heart rate of a patient and heartbeat anomalies caused by forces acting on the patient as a result of external effects can be identified from measured values of the sensor 40.

The invention claimed is:
1. A blood pump comprising:
a pump housing including an axial inlet channel and an outlet channel;
an impeller having an axis of rotation in the pump housing along an axial direction and including a central blade member located at the axis of rotation, an annular sleeve surrounding the central blade member, and a plurality of blades extending between the central blade member and the annular sleeve;
a motor located at the axis of rotation within the pump housing so as to define a downstream bearing gap between the central blade member and the motor, the motor including a motor cover such that an annular flow-through channel is defined between the motor cover and the pump housing, the annular flow-through channel extending in the axial direction and surrounding the motor between the impeller and the outlet channel, wherein blood flowing in the axial direction through the annular flow-through channel contacts the motor cover and the pump housing, the motor operable to drive rotation of the impeller;
a magnetic axial bearing including a rotor permanent magnet integrated in the annular sleeve and a stator permanent magnet positioned in the pump housing, the rotor permanent magnet and the stator permanent magnet each being magnetized in opposing axial directions; and
a flow mechanical radial bearing including a bearing channel positioned between the annular sleeve and the housing wall such that the bearing channel is positioned between the rotor permanent magnet and the stator permanent magnet,
whereby during operation, the magnetic axial bearing and the flow mechanical radial bearing support the impeller such that the impeller does not contact the pump housing or the motor.

2. The pump of claim 1, wherein the impeller further includes an axial inflow channel.

3. The pump of claim 1, wherein the pump includes exclusively passive bearing elements.

4. The pump of claim 1, wherein the rotor permanent magnet and the stator permanent magnet include neodymium-iron-boron.

5. The pump of claim 1, wherein the magnetic axial bearing exerts a tilt restoring force against tilting of the impeller with respect to a plane normal to the axis of rotation.

6. The pump of claim 1, wherein the rotor permanent magnet and the stator permanent magnet are concentrically arranged.

7. The pump of claim 1, wherein the impeller acquires an axial equilibrium in a magnetic field and axially upstream of a downstream wall of the housing, which limits the downstream movement of the impeller.

8. The pump of claim 7, wherein an axially downstream deflection of the impeller, starting from the axial equilibrium, brings about a resulting restoring force applied by the magnetic axial bearing and acting against the deflection.

9. The pump of claim 1, further comprising a rotary face magnetic coupling between the motor and the impeller.

10. The pump of claim 1, wherein the impeller is axially free from contact with the pump housing when stationary.

11. The pump of claim 1, wherein the impeller abuts radially against the pump housing when stationary.

12. The pump of claim 1, further comprising a non-magnetic motor cover.

13. The pump of claim 1, wherein the impeller includes an axial and/or diagonal-axial principal flow channel through the plurality of blades, an axial inflow channel, and the bearing channel includes a feed opening and a discharge opening, wherein the discharge opening is oriented to the inflow channel.

14. The pump of claim 1, wherein an inflow runs substantially axially into the impeller and an outflow runs substantially diagonally from the impeller into the annular flow-through channel.

15. The pump of claim 1, wherein the bearing channel of the flow mechanical radial bearing is separate from a principal flow channel running through the impeller when the pump is operating.

16. The pump of claim 1, wherein during operation, a bearing flow is oriented substantially in the opposite direction to a principal flow.

17. The pump of claim 1, wherein during operation, a bearing flow is fed back into the impeller.

18. The pump of claim 17, wherein during operation, flow discharges into an inflow for the bearing flow from the impeller.

19. The pump of claim 1, wherein during operation, a bearing flow runs predominantly in the axial direction through the bearing channel.

20. The pump of claim 1, wherein the bearing channel is extended flat and, in one dimension perpendicular to its surface, includes an extension of more than 100 μm in length.

21. The pump of claim 1, wherein the bearing channel has an axial length of 1 mm to 20 mm.

22. The pump of claim 1, wherein the impeller has a diameter of 2 mm to 100 mm.

23. The pump of claim 1, wherein a bearing flow during operation accounts for between 10% and 50% of a principal flow through the impeller of about 5 L/min.

24. The pump of claim 1, wherein the flow-mechanical radial bearing exerts a centering force during operation on a circumference of the impeller.

25. The pump of claim 1, wherein a discharge opening of the bearing channel is covered in the axial direction by a radial projection of the pump housing.

26. The pump of claim 1, wherein the magnetic axial bearing is arranged at an axial height of an upstream end of the impeller.

27. The pump of claim 1, further comprising a sensor for determining the magnitude of an axial displacement of the impeller.

28. The pump of claim 27, wherein the sensor is provided outside a channel network with a sensor range inside the channel network.

29. The pump of claim 27, wherein the sensor is separated from a principal channel by a partition.

30. The pump of claim 1, further comprising an evaluation device for calculating or identifying pressure, flow rate, flow fluctuation frequency and/or flow fluctuation anomalies as well as external stresses on a patient.

31. The pump of claim 1, wherein the pump is a centrifugal pump.

32. A method for operating a pump, the pump including:
a pump housing including an axial inlet channel and an outlet channel;
an impeller having an axis of rotation in the pump housing along an axial direction and including a central blade member located at the axis of rotation, an annular sleeve surrounding the central blade member, and a plurality of blades extending between the central blade member and the annular sleeve;
a motor located at the axis of rotation within the pump housing so as to define a downstream bearing gap between the central blade member and the motor, the motor including a motor cover such that an annular flow-through channel is defined between the motor cover and the pump housing, the annular flow-through channel extending in the axial direction and surrounding the motor between the impeller and the outlet channel, wherein blood flowing in the axial direction through the annular flow-through channel contacts the motor cover and the pump housing, the motor operable to drive rotation of the impeller;
a magnetic axial bearing including a rotor permanent magnet integrated in the annular sleeve and a stator permanent magnet positioned in the pump housing, the rotor permanent magnet and the stator permanent magnet each being magnetized in opposing axial directions; and
a flow mechanical radial bearing including a bearing channel positioned between the annular sleeve and the housing wall such that the bearing channel is positioned between the rotor permanent magnet and the stator permanent magnet,
the method comprising:
adjusting a secondary flow through the flow-mechanical radial bearing so that the impeller is radially stabilized against a radial deflection; and
assisting a centering effect of the flow-mechanical radial bearing with a magnetic coupling.

33. The method of claim 32, further comprising:
adjusting a principal flow through the impeller, a magnetic coupling, and a magnetic axial bearing with respect to one another so that the impeller takes on a stable axial equilibrium under constant principal flow.

34. The method of claim 32, further comprising:
driving the impeller at a speed of less than 50,000 rpm.

35. The method of claim 32, further comprising:
pumping a principal flow of about 1 L/min to 10 L/min.

36. The method of claim 32, further comprising:
pumping the secondary flow between about 1 L/min and 3 L/min.

37. The method of claim 32, wherein the secondary flow is between about 10% and about 50% of a principal flow.

38. A blood pump comprising:
a pump housing including an axial inlet channel and an outlet channel;
an impeller having an axis of rotation in the pump housing along an axial direction and including a central blade member located at the axis of rotation, an annular sleeve surrounding the central blade member, and a plurality of blades extending between the central blade member and the annular sleeve;
a motor located at the axis of rotation within the pump housing so as to define a downstream bearing gap between the central blade member and the motor, the motor including a motor cover such that an annular flow-through channel is defined between the motor cover and the pump housing, the annular flow-through channel extending in the axial direction and surrounding the motor between the impeller and the outlet channel, wherein blood flowing in the axial direction through the annular flow-through channel contacts the motor cover and the pump housing, the motor operable to drive rotation of the impeller;
a magnetic axial bearing for operating the blood pump without contact between the impeller and the housing, the magnetic axial bearing including a rotor permanent magnet integrated in the annular sleeve and a stator permanent magnet positioned in the pump housing and concentric to the rotor permanent magnet, the rotor permanent magnet and the stator permanent magnet each being magnetized in opposing axial directions and each being centered at the axis of rotation; and a flow mechanical radial bearing including a bearing channel positioned between the annular sleeve and the housing wall such that the bearing channel is positioned between the rotor permanent magnet and the stator permanent magnet.

39. The pump of claim 38, wherein the pump includes exclusively passive bearing elements.

40. The pump of claim 38, wherein the magnetic axial bearing exerts a tilt restoring force against tilting of the impeller with respect to a plane normal to the axis of rotation.

41. The pump of claim 38, wherein the impeller acquires an axial equilibrium in a magnetic field and axially upstream of a downstream wall of the housing, which limits the downstream movement of the impeller.

42. The pump of claim 41, wherein an axially downstream deflection of the impeller, starting from the axial equilibrium, brings about a resulting restoring force applied by the magnetic axial bearing and acting against the deflection.

43. The pump of claim 38, further comprising a rotary face magnetic coupling between the motor and the impeller.

44. The pump of claim 38, wherein the impeller is axially free from contact with the pump housing when stationary.

45. The pump of claim 38, wherein the impeller abuts radially against the pump housing when stationary.

46. The pump of claim 38, wherein during operation, a bearing flow is oriented substantially in the opposite direction to a principal flow.

47. The pump of claim 38, wherein during operation, a bearing flow is fed back into the impeller.

48. The pump of claim 38, wherein during operation, flow discharges into an inflow for the bearing channel from the impeller.

49. The pump of claim 38, further comprising a sensor for determining the magnitude of an axial displacement of the impeller.

* * * * *